United States Patent
Almog et al.

(10) Patent No.: US 11,578,306 B2
(45) Date of Patent: Feb. 14, 2023

(54) METHODS FOR PROPAGATING MESENCHYMAL STEM CELLS (MSC) FOR USE IN TRANSPLANTATION

(71) Applicant: CELLECT BIOTHERAPEUTICS LTD., Kfar Saba (IL)

(72) Inventors: Tal Almog, Kibbutz Nir Elyau (IL); Shai Yarkoni, Kfar Saba (IL)

(73) Assignee: CELLECT BIOTHERAPEUTICS LTD., KfarSaba (IL)

( * ) Notice: Subject to any disclaimer, the term of this patent is extended or adjusted under 35 U.S.C. 154(b) by 0 days.

(21) Appl. No.: 15/762,956

(22) PCT Filed: Sep. 22, 2016

(86) PCT No.: PCT/IL2016/051053
§ 371 (c)(1),
(2) Date: Mar. 23, 2018

(87) PCT Pub. No.: WO2017/051421
PCT Pub. Date: Mar. 30, 2017

(65) Prior Publication Data
US 2018/0340144 A1  Nov. 29, 2018

Related U.S. Application Data

(60) Provisional application No. 62/222,853, filed on Sep. 24, 2015.

(51) Int. Cl.
*C12N 5/0775* (2010.01)
*C12N 5/07* (2010.01)
*C12N 5/074* (2010.01)
*A61K 35/12* (2015.01)

(52) U.S. Cl.
CPC ............... *C12N 5/06* (2013.01); *A61K 35/12* (2013.01); *C12N 5/0607* (2013.01); *C12N 5/0667* (2013.01); *C12N 2501/25* (2013.01)

(58) Field of Classification Search
CPC .... C12N 5/06; C12N 5/0667; C12N 2501/25; C12N 2501/48; A61K 35/12; A61K 35/28; A61P 9/14; A61P 9/04; A61P 9/00; A61P 43/00; A61P 37/06; A61P 37/02; A61P 19/08; A61P 17/00; A61P 1/04
See application file for complete search history.

(56) References Cited

U.S. PATENT DOCUMENTS

| | | |
|---|---|---|
| 5,851,832 A | 12/1998 | Weiss et al. |
| 2002/0098166 A1 | 7/2002 | Havemann et al. |
| 2010/0040582 A1* | 2/2010 | Askenasy ............ C12N 5/0081 424/93.7 |

FOREIGN PATENT DOCUMENTS

WO  2007/138597 A2  12/2007

OTHER PUBLICATIONS

Solodeev (2018, Cell Death and Disease (2018) 9:695, 13 pages).*
Anderson et al., CD105 (Endoglin)-Negative Murine Mesenchymal Stromal Cells Define a New Multipotent Subpopulation with Distinct Differentiation and Immunomodulatory Capacities, PLOS ONE, (2013), vol. 8, issue 10, pp. e76979—13 pages.
Bunnell et al., "Adipose-derived Stem Cells: Isolation, Expansion and Differentiation", Methods, (2008), vol. 45, No. 2, pp. 115-120.
Dominici et al., "Minimal criteria for defining multipotent mesenchymal stromal cells. The International Society for Cellular Therapy position statement", Cytotherapy, (2006), vol. 8, No. 4, pp. 315-317.
Funcke et al., "TNF-related apoptosis-inducing ligand promotes human preadipocyte proliferation via ERK1/2 activation", FASEB J., (2015), vol. 29, pp. 3065-3075.
Ikebe et al., "Mesenchymal Stem Cells for Regenerative Therapy: Optimization of Cell Preparation Protocols", Hindawi Publishing Corporation, BioMed Research International, (2014), vol. 2014, article id 951512, 11 pages.
Ma et al., "Immunobiology of mesenchymal stem cells", Cell Death and Differentiation, (2014), vol. 21, pp. 216-225.
Mark et al., "Human Mesenchymal Stem Cells Display Reduced Expression of CD105 after Culture in Serum-Free Medium", Hindawi Publishing Corporation, Stem Cells International, (2013), vol. 2013, article id 698076, 8 pages.
Mazar et al., "Cytotoxicity Mediated by the Fas Ligand (FasL)-activated Apoptotic Pathway in Stem Cells", J. Biol. Chem., (2009), vol. 284, pp. 22022-22028.
Rippo et al., "Low FasL levels promote proliferation of human bone marrow-derived mesenchymal stem cells, higher levels inhibit their differentiation into adipocytes", Cell Death and Disease, (2013), vol. 4, pp. e594—10 pages.
Rodrigues et al., "Surface Tethered Epidermal Growth Factor Protects Proliferating and Differentiating Multipotential Stromal Cells from FasL-Induced Apoptosis", Stem Cells, (2013), vol. 31, pp. 104-116.
Schreml et al., "Harvesting human adipose tissue-derived adult stem cells: resection versus liposuction", Cytotherapy, (2009), vol. 11, No. 7, pp. 947-957.
Shoshani et al., "The tissue specific nature of mesenchymal stem/stromal cells: Gaining better understanding for improved clinical outcomes", RNA & Disease, (2015), vol. 2, pp. e780—6 pages.
Yoshimura et al., "Characterization of Freshly Isolated and Cultured Cells Derived From the Fatty and Fluid Portions of Liposuction Aspirates", J. Cell. Physiol., (2006), vol. 208, pp. 64-76.

* cited by examiner

*Primary Examiner* — Valarie E Bertoglio
(74) *Attorney, Agent, or Firm* — Vorys, Sater, Seymour and Pease LLP; Anthony P. Venturino; Maryellen Feehery Hank

(57) ABSTRACT

Provided are methods for propagating mesenchymal stem cells (MSC), and particularly adipose derived stem cells, including incubating isolated cells obtained from a tissue or organ including MSC in a growth medium including an apoptosis inducing agent, under specified conditions. Further provided is an isolated cell population and kits for performing the methods.

6 Claims, 6 Drawing Sheets

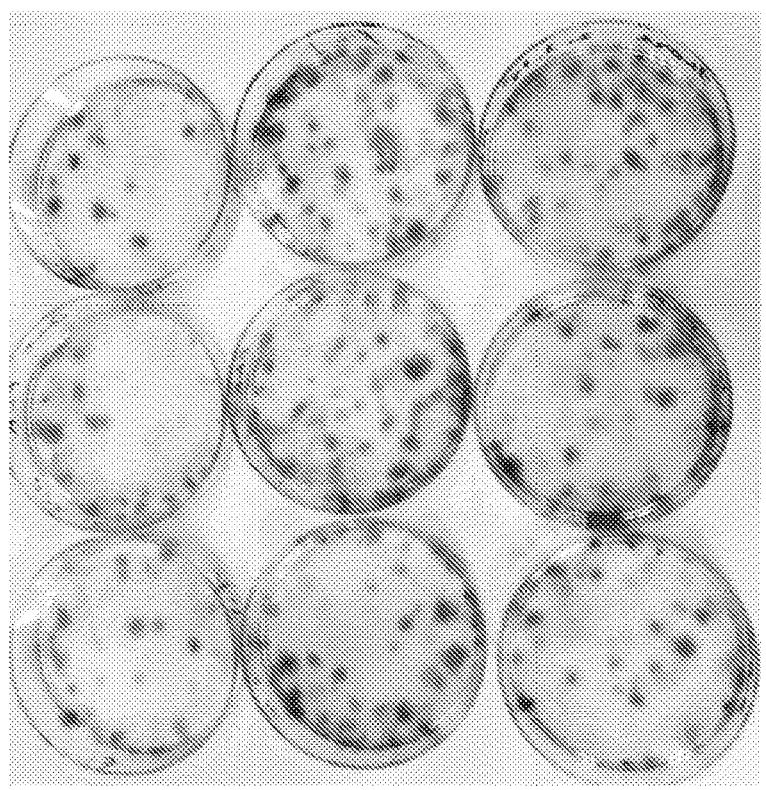
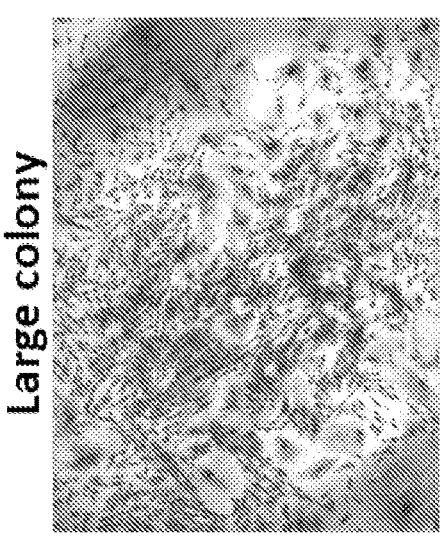
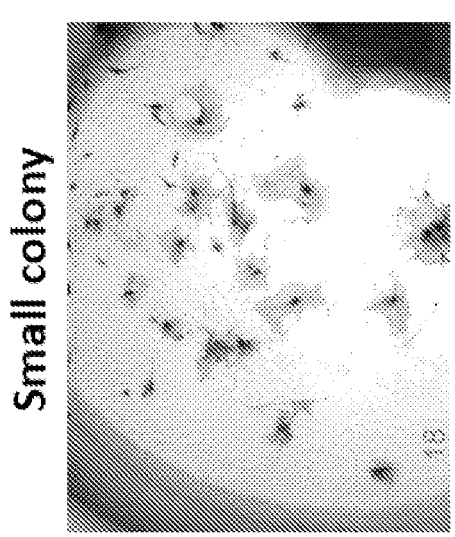
Fig.4A Control
Fig.4B FAS-L treated cells "Long treatment"
Large colony
Small colony
Fig.4C FAS-L treated cells "Short treatment"

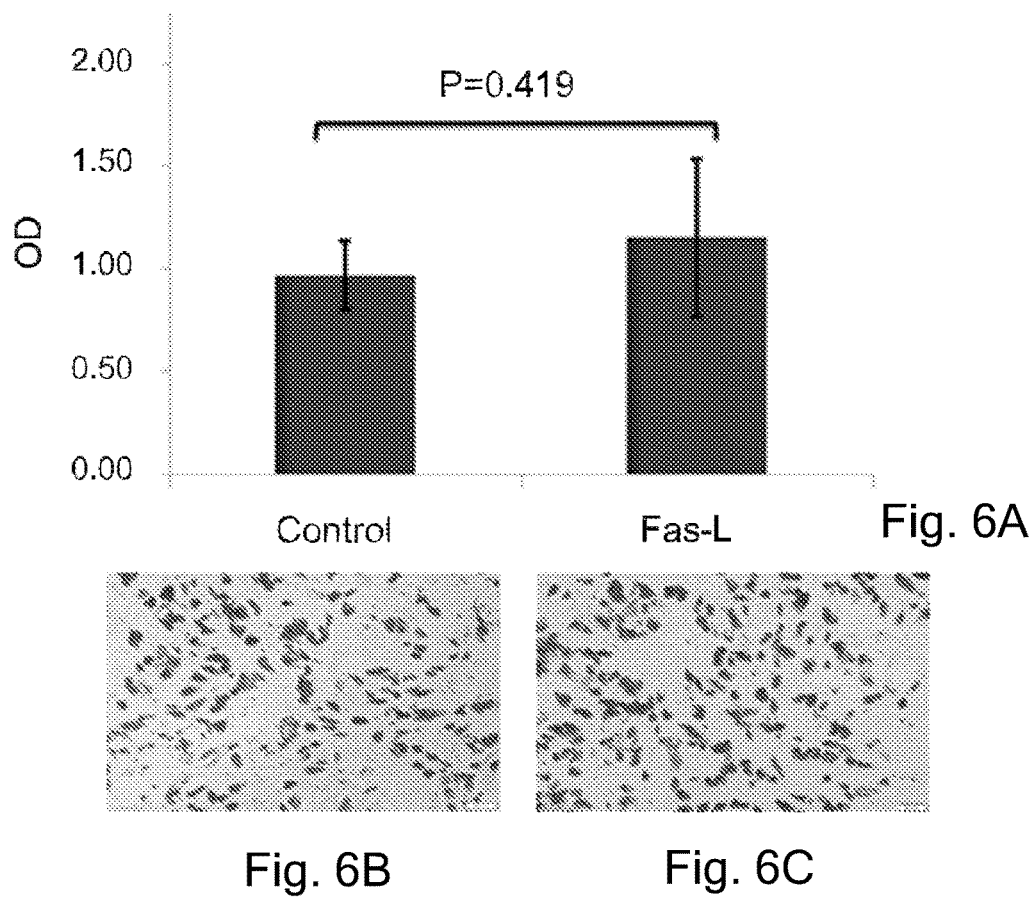
Fig. 6A
Fig. 6B    Fig. 6C
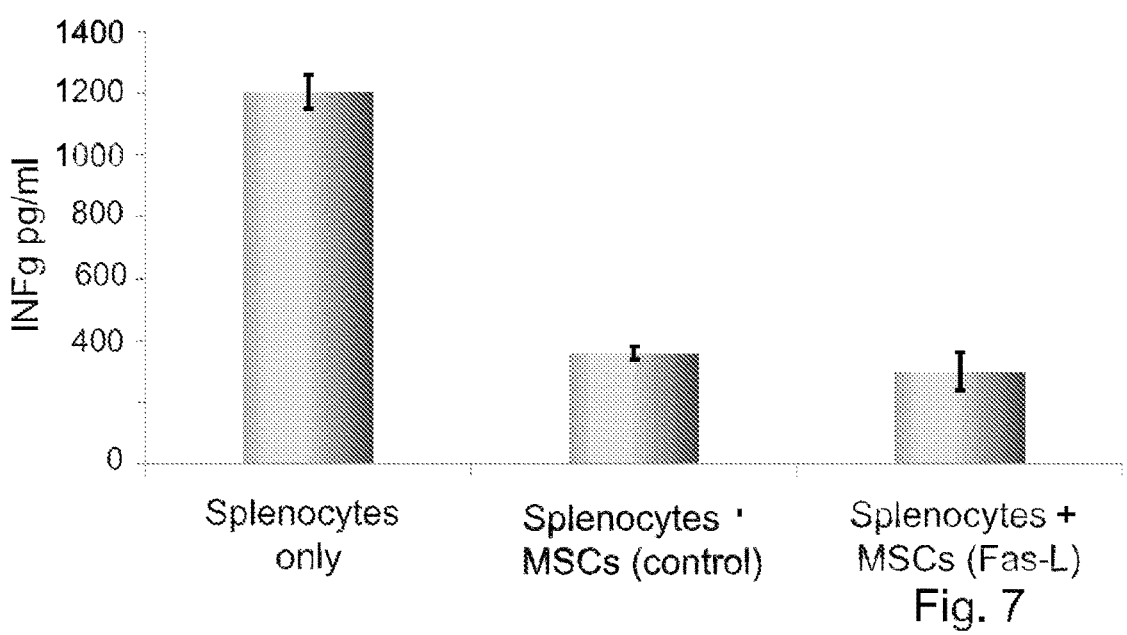
Fig. 7

METHODS FOR PROPAGATING MESENCHYMAL STEM CELLS (MSC) FOR USE IN TRANSPLANTATION

TECHNOLOGICAL FIELD

The invention is in the field of cell transplantation, and in particular the invention provides methods for propagating mesenchymal stem cells in vitro.

BACKGROUND ART

References considered to be relevant as background to the presently disclosed subject matter are listed below:
[1] Bunnell, B. A. et al. (2008) *Methods* 45(2): 115-120.
[2] Shoshani, O. et al. (2015) *RNA and Disease* 2: e780.
[3] Ikebe, C. and Suzuki, K. (2014) *BioMed Research International* Article ID 51512.
[4] Ma, S. et al. (2014) *Cell Death and Differentiation* 21: 216-225.
[5] WO 2007/138597.
[6] Rippo, M. R. et al. (2013) *Cell Death and Disease* 4: e594.
[7] Funcke, J. B. et al. (2015) *FASEB J.* 29:3065-3075.
[8] U.S. Pat. No. 5,851,832.
[9] US 2002/0098166.
[10] Dominici, M. et al. (2006) *Cytotherapy* 8(4): 315-317.
[11] Schreml et al. (2009) *Cytotherapy* 11(7): 947-57.
[12] Yoshimura et al. (2006) *J. of Cellular Physiology* 208: 64-76.
[13] Mark, P. et al. *Stem Cells International* Volume 2013 (2013), Article ID 698076, 8 pages.
[14] Anderson, P. et al. (2013) *PLOS ONE* 8(10): e76979.

Acknowledgement of the above references herein is not to be inferred as meaning that these are in any way relevant to the patentability of the presently disclosed subject matter.

BACKGROUND

Mesenchymal stem cells (MSC) are multipotent progenitor cells that can differentiate into a variety of specific cell types, including adipocytes, osteocytes, and chondrocytes. MSCs persist in adult tissues and retain a broad differentiation potential (1).

While MSCs are most commonly isolated from bone marrow, they may also be isolated from other tissues including adipose tissue, placenta, amniotic fluid and umbilical cord blood. However, studies reported differences in the propagation and differentiation abilities of MSCs that were isolated from different sources (2).

Allogeneic or autologous MSCs may be used for the treatment of various diseases, including graft versus host disease, hematologic malignancies, cardiovascular diseases, neurologic diseases, autoimmune diseases, organ transplantation, and bone or cartilage diseases (3). In addition, the MSCs may be used in cosmetic applications and for plastic surgeries.

Therefore, establishment of protocols for MSCs isolation and expansion is desirable for obtaining an enriched cell population for further clinical use. MSCs isolated from various tissues can be expanded in vitro while maintaining their potential to differentiate into specific cell lineages (4). TNF superfamily members mediate pathways of caspase activation and thereby mediate apoptosis via direct or indirect mechanisms, Pro-apoptotic TNF superfamily regulators include among others TNFα, TNFβ, Fas, Fas-ligand, TNF-related apoptosis-inducing ligand (TRAIL), and tumor necrosis factor-like weak inducer of apoptosis (TWEAK).

The publication WO 2007/138597 (5) relates to a method of selecting stem cells from a heterogeneous population of cells isolated from bone marrow by contacting the population of cells with a pro apoptotic agent. Rippo et al (6) report that low Fas-ligand (FasL) levels promote proliferation of MSCs derived from human bone marrow and higher levels inhibit their differentiation into adipocytes. The authors conclude that the FasL/Fas system has a role in bone marrow MSC biology and may have clinical relevance in osteoporosis. Funcke et al (7) report that TRAIL promotes human preadipocyte proliferation via ERK1/2 activation, and proposed a role for TRAIL in regulating adipose tissue homeostasis.

General Description

In a first of its aspects, the present invention provides a method for propagating mesenchymal stem cells (MSC), the method comprising:
(a) isolating cells from a body tissue or organ; and
(b) incubating the isolated cells obtained in (a) in a growth medium comprising an apoptosis inducing agent for at least 3 days, thereby obtaining a cell population enriched with MSC.

In certain embodiments the method of the invention is performed in vitro.

In certain embodiments the method of the invention is performed with isolated cells and does not involve step (a).

In another aspect, the present invention provides a method for propagating adipose derived stem cells (ASC), the method comprising:
(a) isolating stromal vascular fraction (SVF) cells from a liposuction aspirate; and
(b) incubating the isolated cells obtained in (a) in a growth medium comprising an apoptosis inducing agent for at least 3 days, thereby obtaining a cell population enriched with ASC.

In certain embodiments the MSC or ASC are for use in transplantation.

In certain embodiments, said apoptosis inducing agent is a TNF super family ligand.

In certain embodiments, said apoptosis inducing agent is selected from the group consisting of Fas-ligand (FasL), tumor necrosis factor (TNF) α, TNF-related apoptosis-inducing ligand (TRAIL), tumor necrosis factor-like weak inducer of apoptosis (TWEAK), and a combination thereof.

In a specific embodiment said apoptosis inducing agent is FasL.

In certain embodiments said growth medium further comprises an additional active agent selected from the group consisting of a growth factor, a hormone, a cytokine and any combination thereof.

In other embodiments, said growth medium does not comprise an additional active agent, other than the apoptosis inducing agent.

In one embodiment, said incubation with the apoptosis inducing agent is for between about 3 days to between about 23 days. In certain embodiments, said incubation with the apoptosis inducing agent is for about 3, 5, 7, 10, 14, 17, 20, or 23 days.

In a specific embodiment, said incubation with the apoptosis inducing agent is for 14 days.

In one embodiment, the medium comprising the apoptosis inducing agent is refreshed every 3 days or every 4 days.

In certain embodiment, after isolating the cells (step (a) of the methods disclosed above), the isolated cells are cultured for 1, 2, 3, 4, 5, 6 or 7 days without an apoptosis inducing agent, followed by incubation with an apoptosis inducing agent.

In one embodiment, said apoptosis inducing agent is FasL, and prior to incubation with FasL, the isolated cells are pre-incubated with TNFα.

In one embodiment, said pre-incubation with TNFα is performed for 1-4 days.

In one embodiment, said apoptosis inducing agent is FasL and the concentration of FasL is in the range of about 0.1 ng/ml to about 100 ng/ml.

In one embodiment, following incubation with the apoptosis inducing agent, said apoptosis inducing agent is removed and said cells are allowed to differentiate.

In certain embodiments, said cells are allowed to differentiate into adipocytes, chondrocytes, or osteocytes. Specifically, said cells are incubated in the presence of medium and reagents suitable for the specific lineage differentiation.

In one embodiment, the methods of the invention further comprise transplanting said differentiated cells into a patient in need thereof.

In one embodiment, said cells differentiate into fat tissue, bone tissue or cartilage.

In a specific embodiment, said cells differentiate into fat tissue and said patient is in need of breast restoration.

In another specific embodiment, said cells differentiate into bone tissue and said patient is in need of treatment of orthopedic injuries, bone reconstruction or bone repair.

In another specific embodiment, said cells differentiate into cartilage tissue and said patient is in need of chondrocyte implantation, treatment of meniscus or articular cartilage repair.

In one embodiment, said patient is in need of a cosmetic procedure.

In another embodiment, said transplanting said differentiated cells is for treating a dermatological condition.

In another embodiment, said transplanting said differentiated cells is for alleviating an immune-related disease in a patient. In a specific embodiment, said patient undergoes organ/tissue transplantation.

In one embodiment, said organ transplantation is selected form the group consisting of bone marrow, liver, kidney, blood vessel or heart transplantation.

In one embodiment, said immune-related disease is graft versus host disease (GvHD).

In another embodiment, said transplanting said differentiated cells is for treating stroke or heart failure in a patient.

In another embodiment, said transplanting said differentiated cells is for treating anal or perianal fistulas in a Crohn's disease patient.

In another embodiment, said transplanting said differentiated cells is for blood vessel repair.

In certain embodiments said transplanted differentiated cells are allogeneic or autologous.

In another aspect, the present invention provides a mesenchymal stem cell growth medium comprising a cell culture medium and an apoptosis inducing agent.

In yet another aspect, the present invention provides an article of manufacture comprising:

a. a vessel containing a mesenchymal stem cell growth medium, wherein said mesenchymal stem cell growth medium comprising a cell culture medium and an apoptosis inducing agent; and b. instructions for using the mesenchymal stem cell growth medium for propagating mesenchymal stem cells in vitro.

In a specific embodiment, said mesenchymal stem cells are adipose derived stem cells.

In one embodiment the mesenchymal stem cell growth medium further comprises serum or serum substitutes.

In another aspect, the present invention provides an enriched population of cells obtained by the methods of the invention.

In another aspect said enriched population of cells is for use in a transplantation procedure into a patient in need thereof.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 4A is a photograph showing a large colony. FIG. 4B is a photograph showing a small colony. FIG. 4C is a photograph showing plates with untreated SVF cells (Control, the upper set) treated for twenty days with FasL ("Long treatment", middle set), or treated for three days with FasL ("Short treatment", lower set).

FIG. 5B—control, cells grown without FasL, FIG. 5C—cells grown in the presence of FasL.

FIG. 6A is graph showing Oil Red O staining of MSC grown in culture with an adipogenic medium. The cells were previously exposed to FasL, or unexposed (control). P=0.419, experiments were repeated three times. FIGS. 6B and 6C are photographs showing differentiated adipocytes in culture stained with Oil Red O; FIG. 6B—control, cells grown without FasL, FIG. 6C—cells grown in the presence of FasL.

FIG. 7 is graph showing the amount of interferon gamma (IFNγ) (IFNγ pg/ml) in the medium of activated mouse splenocytes grown in the presence of mesenchymal stem cells (MSC). The MSC were previously exposed to FasL, or unexposed (control).

DETAILED DESCRIPTION OF EMBODIMENTS

Figure 1:
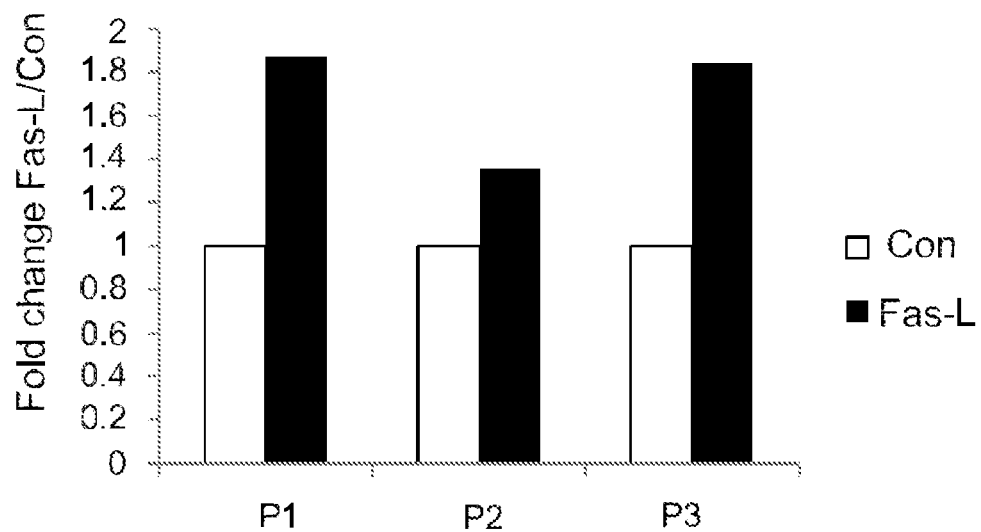
FIG. 1 is a graph showing the change in cell yield upon incubation with 20 ng/ml FasL. The data is shown as the fold change in cells incubated with FasL as compared with control cells that were not exposed to FasL. The data shows results after one, two or three passages (P1, P2, P3) of the cells.

The present invention is based on the surprising observation that stromal vascular fraction (SVF) cells isolated from liposuction aspirates and cultured in vitro in the presence of Fas-ligand (FasL) proliferate rapidly, reach confluence in culture relatively quickly and generate a higher number of colony forming units (CFU), in particular large CFU (i.e. CFU that contain more cells), compared to cells that were not incubated with FasL.

It is therefore assumed that these cells have a high differentiation capacity, despite the relatively short culturing period.

The inventors have thus developed a process for propagating human mesenchymal stem cells from tissue prior to differentiation and then culture expanding the mesenchymal stem cells in a quick and reliable manner to produce high amounts of cells ready to differentiate into a desired differentiated cell.

The invention therefore provides a method for propagating mesenchymal stem cells (MSC), the method comprising:
  (a) isolating cells from a body tissue or organ; and
  (b) incubating the isolated cells obtained in (a) in a growth medium comprising an apoptosis inducing agent for at least 3 days, thereby obtaining a cell population enriched with MSC.

The objective of the method of the invention is to greatly increase the number of mesenchymal stem cells in a short period of time, allow them to differentiate and thereby obtain a cell population that is suitable for transplantation and use for various therapeutic indications, including regenerative therapy.

The invention therefore provides a method for propagating mesenchymal stem cells (MSC) for use in transplantation, the method comprising:
  (a) isolating cells from a body tissue or organ; and
  (b) incubating the isolated cells obtained in (a) in a growth medium comprising an apoptosis inducing agent for at least 3 days, thereby obtaining a cell population enriched with MSC.

The term "Mesenchymal stem cells" (MSCs) as known in the art, relates to multipotent stromal cells that can differentiate into a variety of cell types. MSC were recently defined by the International Society of Cellular Therapy as possessing the following characteristics: (1) plastic-adherent when maintained in standard culture conditions; (2) expression of CD105, CD73 and CD90, and lack of expression of CD45, CD34, CD14 or CD11b, CD79α or CD19 and HLA-DR surface molecules. Third, MSC differentiate to osteoblasts, adipocytes and chondroblasts in vitro (10). Methods for isolating, purifying, and expanding human mesenchymal stem cells in culture are known in the art, see for example U.S. Pat. No. 5,486,359 which concerns mainly the isolation of mesenchymal stem cells from bone marrow.

Bone marrow is the soft tissue occupying the medullary cavities of long bones, some haversian canals, and spaces between trabeculae of cancellous or spongy bone. Studies have suggested that bone marrow contains cells which have the capacity to differentiate into cartilage, bone, and other connective tissue cells (Beresford, J. N.: Osteogenic Stem Cells and the Stromal System of Bone and Marrow, Clin. Orthop. 240:270, 1989). These cells, called pluripotent stromal stem cells or mesenchymal stem cells, have the ability to differentiate into several different types of cell lines (i.e. osteocytes, chondrocytes, adipocytes, etc.) upon activation. However, the mesenchymal stem cells are present in the tissue in very minute amounts with a wide variety of other cells (i.e. erythrocytes, platelets, neutrophils, lymphocytes, monocytes, eosinophils, basophils, adipocytes, etc.)

As used herein the term "body tissue or organ" relates to any tissue or organ in the body of a subject that contains mesenchymal stem cells including, but not limited to, adipose tissue, peripheral blood, bone marrow, dental pulp, amniotic fluid, amnion membrane, chorion membrane, chorion villi, decidua, placenta, umbilical cord, cord blood, Wharton's jelly.

As used herein the term "subject" relates to a mammalian subject, specifically to a human subject.

In certain embodiments, the invention provides a method for propagating mesenchymal stem cells (MSC), comprising incubating isolated cells in vitro in a growth medium comprising an apoptosis inducing agent for at least 3 days, wherein said cells were obtained from a body tissue or organ, thereby obtaining a cell population enriched with MSC.

In one embodiment, the mesenchymal stem cells of the invention are adipose derived stem cells.

Therefore, in a specific embodiment, the invention provides a method for propagating adipose derived stem cells (ASC), the method comprising:
  (a) isolating SVF cells from a liposuction aspirate; and
  (b) incubating the isolated cells obtained in (a) in a growth medium comprising an apoptosis inducing agent for between about 3 days to about 23 days, thereby obtaining a cell population enriched with ASC.

Optionally, said isolation step (a) comprises exposure to a proteolytic enzyme (e.g. collagenases, e.g. collagenase type I) or a mixture of proteolytic enzymes which breaks down tissue (also termed collagenase digestion). Protocols for performing collagenase digestion of cells are well known in the art, and several compounds for performing collagenase digestion are commercially available (e.g. Celase® GMP by Cytori Therapeutics). Collagenase type I can be added at a arrange of between 0.1%-0.3%. A neutral protease, e.g. Dispase II can optionally be added to the digestion reaction. For example, as shown in the Examples below, collagenase can be added at a concentration of 0.375 mg/ml for 60 minutes in agitation at 37° C.

As used here the term "propagating" relates to expansion, multiplication, proliferation or increase in number in vitro of mesenchymal stem cells isolated from a body tissue or organ, e.g. from liposuction aspirates.

The terms "adipose derived stem cells (ASC)" and "adipose derived mesenchymal stem cells (MSC)" are used interchangeably herein and refer to MSCs that were isolated from adipose tissue.

As used herein, "adipose tissue" refers to a connective tissue composed mostly of adipocytes. In addition to adipocytes, adipose tissue contains the stromal vascular fraction (SVF) of cells including preadipocytes, fibroblasts, vascular endothelial cells, a variety of immune cells such as adipose tissue macrophages, stem cells and endothelial precursor cells.

As used herein the term "Stromal vascular Fraction (SVF)" relates to a preparation of adipose tissue that is a rich source of preadipocyes, mesenchymal stem cells (MSC), endothelial progenitor cells, T cells, B cells, mast cells as well as adipose tissue macrophages.

Methods for isolating adipose-derived stem cells or SVF cells from a liposuction aspirate are known in the art (1, 11-12). For example, adipose tissue may be removed from a patient by suction-assisted lipoplasty, ultrasound-assisted lipoplasty, and excisional lipectomy, or a combination thereof. The tissue extraction should be performed in a sterile or aseptic manner.

For suction-assisted lipoplastic procedures, adipose tissue is collected by insertion of a cannula into or near an adipose tissue depot present in the patient followed by aspiration of the adipose tissue into a suction device. A small cannula coupled to a syringe, may be suitable for harvesting relatively moderate amounts of adipose tissue (e.g., from 0.1 ml to a few hundred milliliters). Larger cannulas and automated suction devices may be employed in the procedure if larger volumes of tissue are required.

An exemplary protocol for isolating adipose-derived stem cells or SVF cells from a liposuction aspirate is provided in the Examples section below.

As used herein the term an "Apoptosis inducing agent" (also defined as a "pro-apoptotic agent") refers to an agent (e.g. a chemical or polypeptide) capable of promoting programmed cell death. Exemplary apoptosis inducing agents that may be used in accordance with the present invention include, but are not limited to, tumor necrosis factor (TNF) superfamily ligands.

There are more than 40 distinct ligand-receptor systems that are currently recognized as belonging to the TNF superfamily. Exemplary apoptosis inducing agents that belong to the TNF superfamily and may be used in accordance with the present invention include, but are not limited to Fas-ligand (FasL), TNFα, Trail (Apo2 ligand) and Tweak (Apo3 ligand). Such TNF superfamily apoptosis inducing agents may be recombinant polypeptides, biochemically synthesized or purified from cell extracts. They may be administered as monomer, dimer or multimer forms.

Thus in some embodiments the apoptosis inducing agent in accordance with the present disclosure is a TNF super family ligand. In further embodiments the apoptosis inducing agent is selected from the group consisting of FasL, TNFα, TRAIL and TWEAK.

In a specific embodiment the apoptosis inducing agent is FasL. Non-limiting examples of FasL for use in accordance with the invention include superFasL, APO010 or Mega-FasL (R&D), all of which are hexamers of FasL. The hexamer form of FasL is 100 fold more active than the trimer. Additional forms of FasL, such as Fc-FasL or FasL monomers, are also encompassed by the invention.

The concentration of the apoptosis inducing agent in the medium is in the range of about 1 ng/ml and about 100 ng/ml w/v, for example 1 ng/ml, 5 ng/ml, long/ml, 20 ng/ml, 30 ng/ml, 40 ng/ml, 50 ng/ml, 60 ng/ml, 70 ng/ml, 80 ng/ml, 90 ng/ml or 100 ng/ml w/v of the apoptosis inducing agent. In a specific embodiment whereby the apoptosis inducing agent is FasL the medium comprises between about 1 ng/ml and about 100 ng/ml w/v FasL, for example 1 ng/ml, 5 ng/ml, 10 ng/ml, 20 ng/ml, 30 ng/ml, 40 ng/ml, 50 ng/ml, 60 ng/ml, 70 ng/ml, 80 ng/ml, 90 ng/ml or 100 ng/ml w/v FasL.

As indicated above the method for propagating mesenchymal stem cells (MSC) comprises incubating the cells isolated from a body tissue or organ in a growth medium comprising an apoptosis inducing agent for the indicated period of time. As known in the art, the term "incubating" refers to growing and maintaining the cells at an appropriate temperature and gas mixture (typically, 37° C., 5% $CO_2$ for mammalian cells) in a cell incubator. As used in the context of the present invention, "incubating the isolated cells in a growth medium comprising an apoptosis inducing agent", means contacting the isolated cells with the apoptosis inducing agent.

In some embodiments the method according to the present disclosure is where the incubation with the apoptosis inducing agent is for at least 3 days, namely for three days or more. In specific embodiments the incubation is for between about 3 days to about 23 days, specifically for about 3, 5, 7, 10, 14, 17, 20, or 23 days.

In other embodiments the incubation with the apoptosis inducing agent is for 14 days and in a specific embodiment, the apoptosis inducing agent is FasL and the isolated cells are incubated with FasL for 14 days whereby the medium is replenished every 3-4 days. In a specific embodiment the FasL is provided in an amount of 50 ng/ml.

In some embodiments the medium comprising the apoptosis inducing agent is refreshed every 3 days or every 4 days, namely it is replaced by a fresh medium having the same content.

In some embodiments incubation with FasL commences 1-7 days after the cells are isolated. In specific embodiments the method according to the present disclosure is wherein after step (a) the isolated cells are cultured for 1, 2, 3, 4, 5, 6 or 7 days without an apoptosis inducing agent, followed by incubation with an apoptosis inducing agent.

In one specific embodiment the incubation with FasL commences three days after the cells are isolated. Namely, according to this embodiment, the cells are incubated in medium without FasL for three days after isolation.

In one embodiment, prior to incubation with FasL, the isolated cells are pre-incubated with a molecule that can affect the cellular response to FasL (i.e. to sensitize the cells to its effect), for example by increasing the expression of Fas. TNFα is an example of such a sensitizing molecule.

Therefore in some embodiments the method according to the present disclosure is wherein the apoptosis inducing agent is FasL, and wherein prior to incubation with FasL, the isolated cells are pre-incubated with TNFα. In further specific embodiments the pre-incubation with TNFα is performed for 1-4 days.

In some embodiments the method according to the present disclosure is where the apoptosis inducing agent is FasL and the concentration of FasL is in the range of about 0.1 ng/ml to about 100 ng/ml.

In certain embodiments, in addition to the at least one apoptosis inducing agent the cells are incubated with an additional active agent selected from the group consisting of a growth factor, a hormone, a cytokine and any combination thereof. In a specific, non-limiting example the cells may be incubated with one or more antagonists of death receptor 3 (DR3, also known as TNFRSF25). Such antagonists include, but are not limited to, anti DR3 antibodies which are commercially available for example from abcam, R&D Systems and other suppliers.

As shown in the Examples below, treatment with Fas-ligand for 14 days increased the percentage of $CD31^-$/$CD34^+$ cells compared to untreated cells. In addition, the treatment with Fas-ligand induced a shift from $CD29^+$/$CD105^+$ to $CD29^+$/$CD105^-$.

The term CD34 as known in the art refers to a cluster of differentiation in a cell surface glycoprotein and functions as a cell-cell adhesion factor. It may also mediate the attachment of stem cells to bone marrow extracellular matrix or directly to stromal cells. Cells expressing surface glycoprotein 34 ($CD34^+$ cells) are generally found in the umbilical cord and bone marrow as hematopoietic cells, a subset of mesenchymal stem cells, endothelial progenitor cells and more. CD34$^+$ cells are considered to be less differentiated cells if they do not express CD31 (i.e. CD31$^-$ cells) that is normally found on endothelial cells, platelets, macrophages and Kupffer cells, granulocytes, T/NK cells, lymphocytes, megakaryocytes, osteoclasts, neutrophils.

The term CD105 (endoglin) as known in the art refers to a proliferation-associated and hypoxia-inducible protein abundantly expressed in angiogenic endothelial cells. It was reported that human mesenchymal stem cells display reduced expression of CD105 after culture in serum-free medium, and that the expression of CD29 in these cells is high (13). In addition, it was reported that CD105$^-$ murine ASCs had greater capacity to differentiate into adipocytes and osteocytes compared to CD105$^+$ ASCs and were better at inhibiting T cell proliferation in vitro (14).

Therefore, without wishing to be bound by theory the incubation with the apoptosis inducing agent caused a shift in the population of cells towards a less differentiated state and increased their "stemness".

As indicated above the present disclosure provides a method for propagating mesenchymal stem cells (MSC) for use in transplantation as herein defined, thereby obtaining a cell population enriched with MSC. As used herein the term "enriched" refers to enhancing, augmenting or increasing the relative number of MSC in the cell population to at least about 50%, 55%, 60%, 65%, 70%, 75%, 80%, 85%, 90%, 95% 96%, 97%, 98%, 99% or about 100% of the cell population.

Upon completion of the incubation period with the apoptosis inducing agent the propagated cells are removed from the culture, reseeded and may now differentiate to any one of adipocytes, chondrocytes, osteocytes, fibroblasts, or myocytes depending on the culturing conditions. The conditions for differentiating into each of the desired cell types are well known in the art and include incubation of the cells in a medium that contains specific reagents.

Therefore in some embodiments the method according to the present disclosure is where following incubation with the apoptosis inducing agent, said apoptosis inducing agent in removed and said cells are allowed to differentiate. In other specific embodiments the cells are allowed to differentiate into adipocytes, chondrocytes, or osteocytes, and are termed herein the "differentiated cells".

As used herein the term "allowed to differentiate" relates to the incubation of the cells under conditions suitable for differentiation into any of the desired cell types. Such conditions are well known in the art and include in particular incubation in a medium that contains a typical set of reagents.

For example, mesenchymal stem cell adipogenesis medium contains reagents that readily differentiate mesenchymal stem cells to an adipogenic lineage (i.e. dexamethasone, IBMX, insulin and indomethacin). Such media are commercially available, for example, Lonza's hMSC Adipogenic Differentiation BulletKit™ Medium or Stemcell Technologies' MesenCult™ Adipogenic Differentiation Medium. Differentiation into adipocytes can then be validated by a variety of methods providing a quantitative value related to the amount of adipogenic differentiation. Other media may be used to induce differentiation to other cell types (e.g. Mesenchymal Stem Cell Chondrogenic Differentiation Medium, Mesenchymal Stem Cell Osteogenic Differentiation Medium or Mesenchymal Stem Cell Neurogenic Differentiation Medium (Promocell). The propagated ASC may also trans-differentiate into cells of germ-origin other than their own, e.g. into cardiomyogenic, endothelial (vascular), pancreatic (endocrine), neurogenic, and hepatic trans-differentiation, while also supporting haematopoiesis.

In further embodiments the method according to the present disclosure further comprises transplanting the differentiated cells into a patient in need thereof.

As used herein, the term "patient in need thereof" relates to a subject suffering from a disease that may be ameliorated, cured, treated, or having its symptoms alleviated by transplanting the differentiated cells.

Therefore, the differentiated cells may be used for transplantation in a plethora of clinical applications as well as cosmetic applications and plastic surgeries, for example in the following indications that are currently in Phase III/IV clinical trials: Breast reconstruction (restoration), premature ovarian failure, Complex perianal fistula, Anal Fistula and Crohn's disease. ASCs can also be used for cell banking. Additional applications include skin regeneration, dermatological conditions, hepatic regeneration, muscle regeneration, blood vessel repair, treatment of orthopedic injuries, bone reconstruction or bone repair, chondrocyte implantation, treatment of meniscus or articular cartilage repair and treatment of osteoporosis.

The differentiated cells of the invention may also be used for immunosuppression. For example for alleviating graft versus host disease (GvHD) in patients that undergo concomitant organ transplantation, e.g. bone marrow, liver, kidney, blood vessel or heart transplantation. In other embodiments the differentiated cells in accordance with the invention can be used for treating stroke or heart failure.

The transplantation can be allogeneic or autologous.

The term "transplantation" as herein defined refers to transferring the differentiated cells to a patient in need thereof by surgery or injection. The donor and the recipient can be a single individual or different individuals. In such cases the transplant is autologous or allogeneic, respectively. When allogeneic transplantation is practiced, regimes for reducing implant rejection should be undertaken. Such regimes are currently practiced in human therapy and are well known in the art.

The following are examples of cells of mesenchymal origin that are used as an external source of cells for replenishing missing or damaged cells of an organ: U.S. Pat. No. 5,736,396 describes introducing culture-expanded lineage-induced mesenchymal stem cells into the original, autologous host, for purposes of mesenchymal tissue regeneration or repair.

U.S. Pat. No. 4,642,120 provides compositions for repairing defects in cartilage and bones. These are provided in gel form either as such, or embedded in natural or artificial bones.

Transplantation of the differentiated cells can be performed using any method known in the art and at the physician's discretion based on the patient's therapeutic indication. For example, the differentiated cells may be injected at the site of a tissue defect (e.g. a skeletal defect), or incubated in vitro with a biocompatible scaffold or matrix and implanted with the scaffold at the site of the defect.

The differentiated cells of the invention may also be employed in gene therapy. For successful long-term gene therapy, a high frequency of genetically modified cells stably expressing a desired foreign gene is required. Accordingly, the differentiated cells of the present invention can be modified to express a gene product.

As used herein, the term "gene product" refers to proteins, peptides and functional RNA molecules (i.e. polynucleotides). Examples of such gene products include insulin, amylase, protease, lipase, trypsinogen, chymotrypsinogen, carboxypeptidase, ribonuclease, deoxyribonuclease, triaclyglycerol lipase, elastase, amylase, blood clotting factors such as blood clotting Factor VIII and Factor IX, UDP glucuronyl transferase, ornithine transcarbanoylase, and cytochrome p450 enzymes, and adenosine deaminase, for the processing of serum adenosine or the endocytosis of low density lipoproteins, serum thymic factor, thymic humoral factor, thymopoietin, gastrin, secretin, cholecystokinin, somatostatin, serotonin, and substance P.

In another one of its aspects the present disclosure provides a mesenchymal stem cell growth medium comprising a cell culture medium and an apoptosis inducing agent.

A "cell culture medium" or a "growth medium" as herein defined refers to a liquid or gel designed to support the growth of cells. Different types of media are used for growing different types of cells. Examples for cell culture media encompass Dulbecco's Modified Eagle Medium (DMEM) and variants thereof, F10 Nutrient Mixture, Haas F12 Nutrient Mixture, Minimum Essential Media (MEM). RPMI Media 1640 and Iscove's Modified Dulbecco's Medium (IMDM).

All these media are well known and commercially available. For example, DMEM typically includes amino acids, inorganic salts, glucose, phenol red, Hepes sodium pyruvate, and vitamins. The media are often supplemented with antibiotic/antimycotic agents such as penicillin, streptomycin and amphotericin B. The media may include varying glucose contents. In one embodiment the medium has high glucose content, e.g. High glucose DMEM by Gibco.

The cell culture medium may further comprise serum.

The term "serum" or "sera" in the context of the present disclosure refers to a supplement added to cell culture media that provides a broad spectrum of macromolecules, carrier proteins for lipid substances and trace elements, attachment and spreading factors, low molecular weight nutrients, and hormones and growth factors. Typically sera are isolated from mammalian blood preparations. A non-limiting example of a serum suitable for use in connection with the present invention is Fetal Calf serum (FCS) or Fetal Bovine Serum (FBS). Serum substitutes may also be used. The term "serum substitute" relates to serum replacements containing proteins necessary to support cell growth in culture, for example serum substitutes may comprise purified, preferably heat-treated serum albumin, transferrin and insulin. Such proteins may be of any origin, they may be for example mammalian proteins, e.g. bovine serum albumin, transferrin and insulin. Such serum substitutes are commercially available, for example from Sigma-Aldrich. The concentration of the serum in the medium is in the range commonly used for growing cells, namely between about 1% and about 20%. In a specific embodiment the concentration of the serum is about 10% volume/volume. In a further specific embodiment the medium comprises 10% FCS or FBS, e.g. Fetal Bovine Serum by Hyclone™.

The apoptosis inducing agent used in the context of the mesenchymal stem cell growth medium are as herein defined. namely an agent capable of promoting programmed cell death. As indicated above exemplary apoptosis inducing agents that may be used include, but are not limited to, tumor necrosis factor (TNF) superfamily ligands, e.g. FasL, TNFα, Trail (Apo2 ligand) and Tweak (Apo3 ligand). The concentration of the apoptosis inducing agent in the medium is in the range of about 1 ng/ml and about 100 ng/ml w/v, for example 1 ng/ml, 5 ng/ml, long/ml, 20 ng/ml, 30 ng/ml, 40 ng/ml, 50 ng/ml, 60 ng/ml, 70 ng/ml, 80 ng/ml, 90 ng/ml or 100 ng/ml w/v of the apoptosis inducing agent. In a specific embodiment the apoptosis inducing agent is FasL. In a further specific embodiment the medium comprises between about 1 ng/ml and about 100 ng/ml w/v FasL, for example 1 ng/ml, 5 ng/ml, 10 ng/ml, 20 ng/ml, 30 ng/ml, 40 ng/ml, 50 ng/ml, 60 ng/ml, 70 ng/ml, 80 ng/ml, 90 ng/ml or 100 ng/ml w/v FasL.

The mesenchymal stem cell growth medium of the invention may further comprise additional components suitable for cells growth including but not limited to growth factors, cytokines, antibiotics and carriers.

The mesenchymal stem cell growth medium of the invention may be prepared and stored at 4° C. until use and warmed to 37° C. prior to use. In still another one of its aspects the present disclosure provides an article of manufacture comprising:

a. a vessel containing a mesenchymal stem cell growth medium, wherein said mesenchymal stem cell growth medium comprising a cell culture medium and an apoptosis inducing agent; and b. instructions for using the mesenchymal stem cell growth medium for propagating mesenchymal stem cells.

In a specific embodiment said growth medium further comprises serum or a serum substitute.

The term "vessel" as herein defined refers to a container, bag, beaker, bottle, bowl, box, bioreactor, can, flask, or vial that may be used for containing and storing the mesenchymal stem cell growth medium as herein defined.

The term "about" as herein defined indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

EXAMPLES

Without further elaboration, it is believed that one skilled in the art can, using the preceding description, utilize the present disclosure to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook & Russell, 2001.

Standard medicinal chemistry methods known in the art not specifically described herein are generally followed essentially in the series "Comprehensive Medicinal Chemistry" by various authors and editors, published by Pergamon Press.

Experimental Procedures

Liposuction Aspirates

Liposuction aspirates were obtained using IRB-approved protocol from obese or formerly obese donors who underwent liposuction, after informed consent, as detailed in Yoshimura, K. et al. 2006, J Cellular physiology 208:64-76. Liposuction aspirates primarily include saline solution, blood and adipose tissue fragments.

Liposuction aspirates were separated into two portions by centrifugation at 1200 rpm for 5 minutes: a fatty floating adipose portion (also termed "lipoaspirate") and a fluid portion. The fatty portion was aspirated into a clean tube. Cells isolated from the fatty portion are termed "processed lipoaspirate cells" (PLA, 0.6 million cells/1 ml liposuction aspirate) and cells isolated from the fluid portion are termed "liposuction aspirate fluid cells" (LAF, 0.06 million cells/1 ml liposuction aspirate).

Obtaining Stromal Vascular Fraction Cells from Processed Lipoaspirate Cells

Cells isolated from the fatty portion (PLA cells) were washed with phosphate buffered saline (PBS) and centrifuged for 5 min at 1200 rpm. The cells were re-suspended and digested by collagenase (0.375 mg/ml, Sigma Aldrich) for 60 minutes in agitation at 37° C. Then collagenase was neutralized by adding 10% fetal calf serum (FCS) and the stromal vascular fraction (SVF) cells were separated from the fat and fat cells by a further centrifugation step of 15 min at 1400 rpm. Next, SVF cells were counted and plated at a density of $2 \times 10^5$ cells per 6 cm dishes or at a density of $2 \times 10^5$ cells per well in 6 well plates.

Cell Propagation in the Presence of FasL

SVF cells isolated from different lipoaspirates (the fatty portion) obtained from different donors were incubated at 37° C., 5% $CO_2$ in a cell incubator in the presence of Fas-ligand under the conditions described below at several repeats. An exemplary incubation protocol comprised seeding cells on eight plates, where four plates were incubated with Dulbecco's Modified Eagle Medium (DMEM) supplemented with 10% FCS and Fas-ligand at 50 ng/ml (Enzo life sciences) and four plates were incubated with DMEM supplemented with 10% FCS, as control.

Alternatively, six wells were seeded with SVF cells. In such case three wells were incubated with DMEM supplemented with 10% FCS and Fas-ligand at 50 ng/ml and three wells were incubated with DMEM supplemented with 10% FCS, as control.

The medium was changed simultaneously in both the control and the treated groups, every ~72 hours. At ~14 days post seeding, when both treated and untreated plates reached a confluent state, cells were removed from the plate by trypsin and were counted with an automated cell counter. Each plate/well was counted separately. Additional parameters were evaluated for the tested cells, for example the number of viable cells and dead cells and the size and number of colony forming units. Cells were also examined for surface molecule expression using flow cytometry, as detailed below.

SVF cells isolated from different lipoaspirates (the fatty portion) obtained from different donors were also incubated in the presence of Fas-ligand as described above for a shorter period of time, namely from seeding (0 h) for 72 hours (until the first medium replacement).

Flow Cytometry

For FACS (fluorescence activated cell sorter) analysis, the cells were trypsinized, washed with PBS and resuspended in PBS. The cells were divided into FACS tubes ($1 \times 10^5$ cells/tube) and stained with ViViD amine reactive dye (LIVE/DEAD® fixable violet dead cell stain), 1.5 μl/sample, for 30 min at 37° C. in the dark. After washing, the cells were incubated with a 6-color panel containing:

- 5 μl of PE/Cy7 Anti-Human CD73 (BioLegend, San Diego, Calif., USA)
- 5 μl of Alexa Fluor 488 Anti-Human CD29 (BioLegend, San Diego, Calif., USA)
- 5 μl of PE Anti-Human CD34 (BioLegend, San Diego, Calif., USA)
- 5 μl of APC Anti-Human CD105 (BioLegend, San Diego, Calif., USA)
- 5 μl of APC-eFluor 780 Anti-Human CD31 (eBioscience, San Diego, Calif., USA)
- 5 μl of BV650 Anti-Human CD45 (BD Biosciences, San Diego, Calif., USA) for 30 min at 37° C. in the dark.

Labeled cells were analyzed using a BD FACS Canto II flow cytometer (Becton Dickinson, San Jose, Calif., USA).

Annexin V Staining

The cells were washed twice with cold BioLegend Cell Staining Buffer (Cat. No 420201) and then resuspended in Annexin V Binding Buffer (Cat. No 422201) at a concentration of $1 \times 10^6$ cells/ml. 100 μl of cell suspension were transferred into 5 ml test tubes. 5 μl of APC Annexin V were added, followed by addition of 10 μl of PI solution (Cat. No 421301) or 7-AAD (Cat. No 420403/420404). The cells were vortexed gently, and incubate for 15 min at room temperature (25° C.), in the dark. 400 μl Annexin V Binding Buffer (Cat. No. 422201) was added to each tube and analyzed by flow cytometry.

Giemsa Staining

Colonies were fixed with 100% methanol, washed and Giemsa stained, followed by another wash and viewed under a microscope.

Example 1 Culturing Stromal Vascular Fraction (SVF) Cells in the Presence of FasL SVF cells from the fatty portion of liposuction aspirates were obtained and seeded as described above. The cells were then divided into three experimental groups: one group of cells was incubated in the presence of FasL (50 ng/ml) for 72 hours (3 days), another group of cells was incubated in the presence of FasL at the above concentration for about 14 days and the third group was incubated without FasL, and served as a control. The resulting cell population was analyzed and the results are presented below.

Cell Counts

At 14 days post seeding, both treated and untreated plates reached a confluent state (P0). Cells were removed from the plate by trypsin and were counted with an automated cell counter (each plate was counted separately). The number of viable cells obtained for each one of the tested groups is presented in table 1 below.

TABLE 1

Cell counts of cells incubated in the presence of Fas-ligand for 3 days or 14 days

| Experimental group | Control | FASL treatment 14 days | FASL treatment 3 days |
|---|---|---|---|
| Number of cells Million/dish | 0.43 ± 0.05 | 0.66 ± 0.09 | 0.32 ± 0.04 |

As evident from table 1, the number of cells in the group that was treated with FasL for 14 days was about 1.5 times higher (P=0.0043) than the number of cells in the control group and 2-fold higher than the number of cells in the group that was treated with FasL for 3 days.

The effect of FasL treatment on the number of cells was even more pronounced when the cells were seeded in 24 well plates at a concentration of $1.5 \times 10^4$ cells/well, as shown in table 2 below. Under these conditions, the number of cells in the group that was treated with FasL for 14 days was about 2.5 times higher (P=0.003) than the number of cells in the control group.

TABLE 2

Cell counts of cells incubated in the presence of Fas-ligand and plated in 24 wells plates

| Experimental group | Control | FASL treatment 14 days |
|---|---|---|
| Number of cells Million/well | 0.094 ± 0.01 | 0.24 ± 0.05 |

Adipose derived stem cells (ASCs, also termed herein mesenchymal stem cells (MSCs)) were passaged several times. Upon reaching confluence the cells were trypsinized and re-cultured for one, two or three cell passages (termed P1, P2 or P3). Each culturing period took about 10-14 days, and the cells were passaged when 80-90% of the cells reached confluence. The cells became bigger with each passage. At each tested passage, after the cells reached ~90% confluence they were treated with 20 ng/ml FasL for 6 days. The MSCs were then dissociated by trypsinization and counted using a cell counter. As can be seen in FIG. 1, FasL treatment increased the number of MSCs as compared with controls that were not incubated with FasL, regardless of the number of passages that the cells went through. The number of cells increased by 20-80%.

Figure 2:
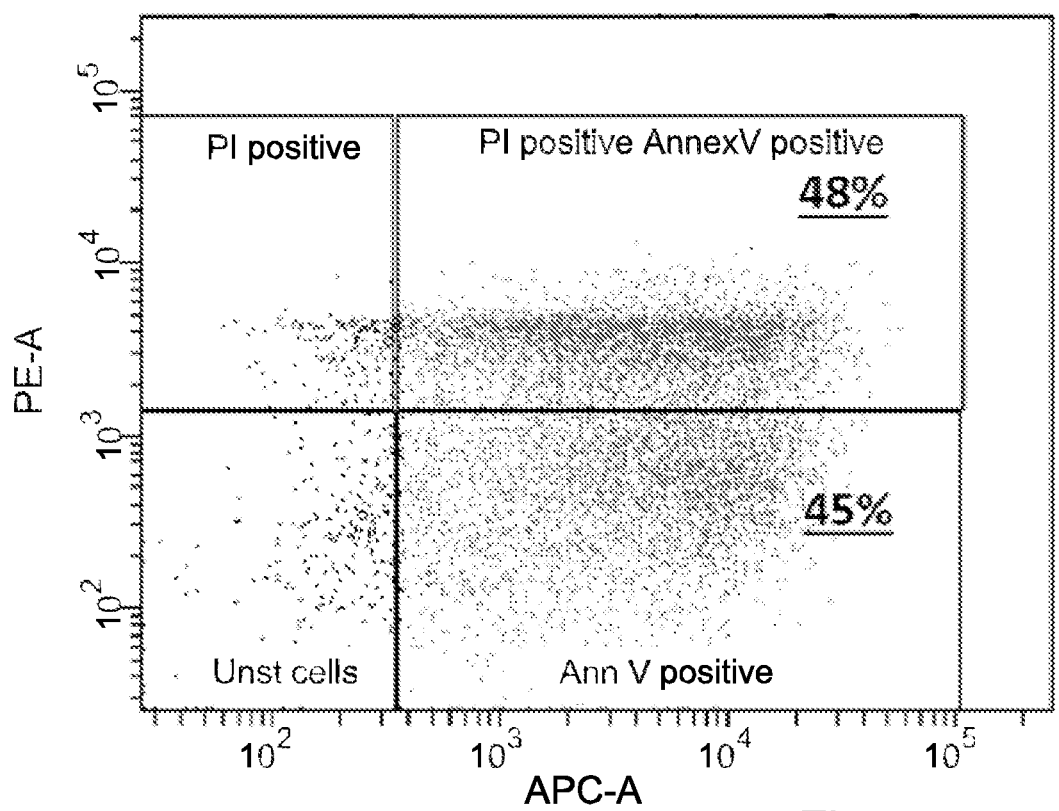
FIG. 2 is a schematic representation showing fluorescent staining of floating SVF cells collected after 14 days of treatment in culture with FasL. The cells were stained with allophycocyanin (APC) Annexin V (shown on the Horizontal axis) and phycoerythrin (PE) PI (shown on the Vertical axis) and fluorescence was measured using a flow cytometer. Unst cells—unstained.

In addition, following 14 days in culture the floating cells were collected and stained with fluorescently labeled Annexin V which is an apoptosis detection marker and with propidium iodide (PI) which is a fluorescent marker of degenerating cells to evaluate the number of dead cells in the cultures. The analysis was performed using a flow cytometer. As shown in FIG. 2 staining of cells with Annexin V and PI indicated that 93% of the cells that were treated with FasL were undergoing early or late apoptosis. Apparently, the number of dead cells in the group treated with FasL for 14 days is 14 times higher than in the other groups.

Without wishing to be bound by theory, these results suggest that incubation with FasL induces high rates of apoptotic cell death in susceptible cells, thus enriching the culture with cells which can proliferate more robustly and also generate large colony forming units as will be shown below.

Surface Molecule Expression

Expression of surface molecules was examined using flow cytometry, performed as detailed above. As shown in table 3 below, the treatment with Fas-ligand for 14 days increased the percentage of $CD31^-/CD34^+$ cells compared to untreated cells. In addition, the treatment with Fas-ligand for 14 days induced a shift from $CD29^+/CD105^+$ to $CD29^+/CD105^-$ with passage, which was not seen in the control group.

The cells that were obtained have mesenchymal stem cells MSC characteristics.

Figure 3A:
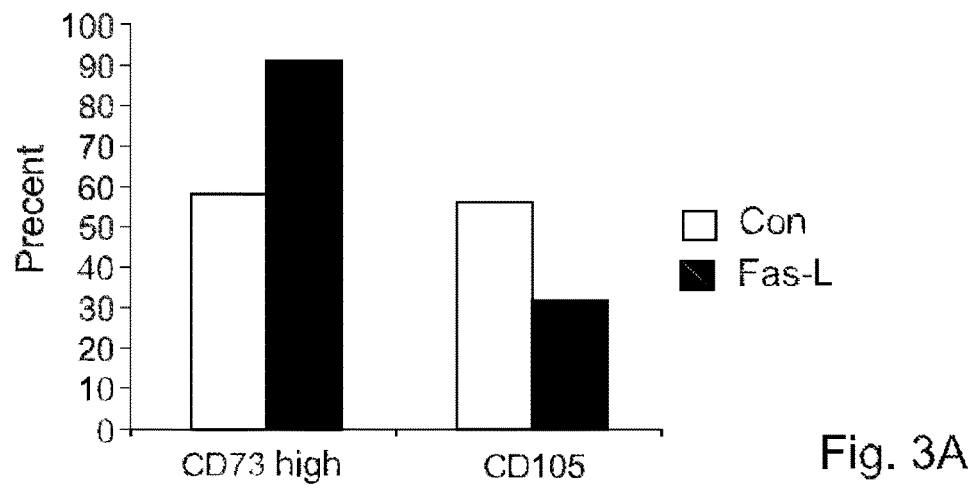
FIG. 3A is a graph showing the percentage of fluorescently stained MSCs that were cultured without FasL (control) or with FasL. The staining was analyzed using a flow cytometer.
Figure 3B:
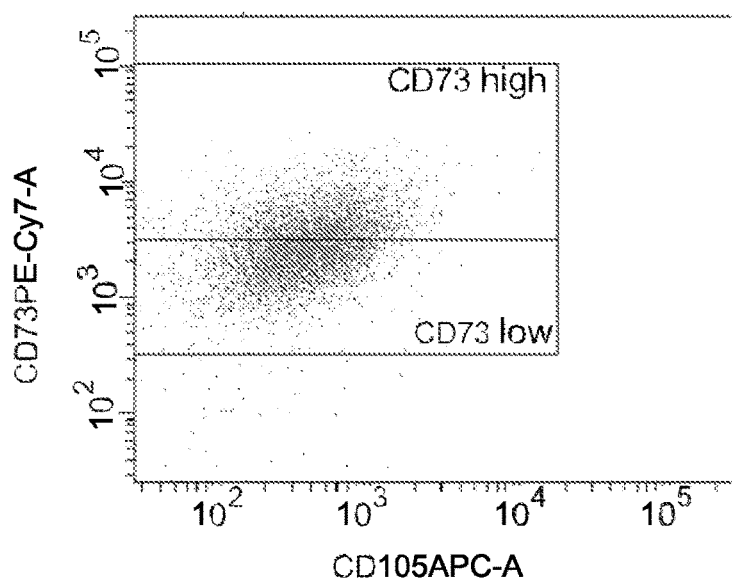
FIGS. 3B and 3C are schematic representations showing fluorescent staining of MSCs that were cultured without FasL (control) [FIG. 3B] or with FasL [FIG. 3C]. The cells were stained with antibodies directed against CD105 (shown on the Horizontal axis) and CD73 (shown on the Vertical axis). Cells were divided to those expressing high or low CD73.
Figure 3C:
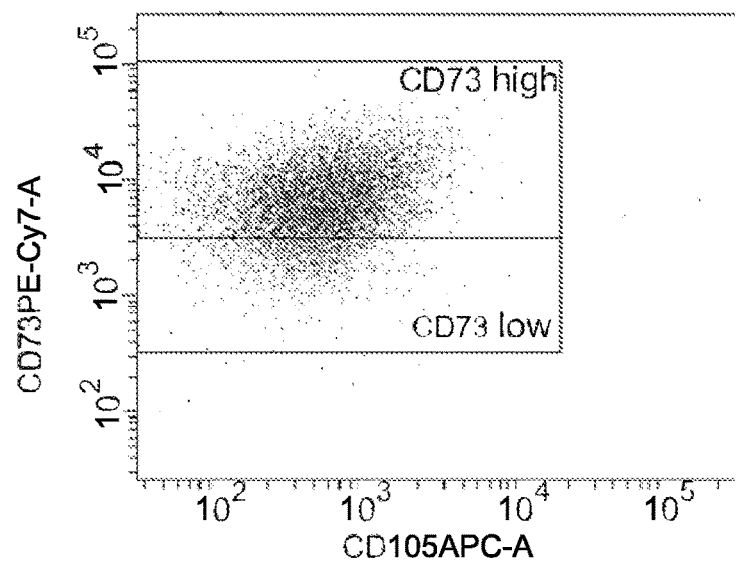

MSC were cultured with or without FasL since P0. MSC Surface markers CD73 (Biolegend, San Diego, Calif., USA) and CD105 (Biolegend, San Diego, Calif., USA) were analyzed by flow cytometry according to manufacturer's instructions. As can be seen in FIG. 3 FasL treatment at P0 leads to changes in cell subpopulations within the growing MSC. The treatment nearly doubled the percentage of MSC expressing CD73. At the same time FasL treatment decreased the percentage of CD105-positive cells nearly by half. Namely FasL treatment increases CD73 high population, and reduces CD105 (+) cells.

Characterization of Colony Forming Units (CFU)

Figure 4D:
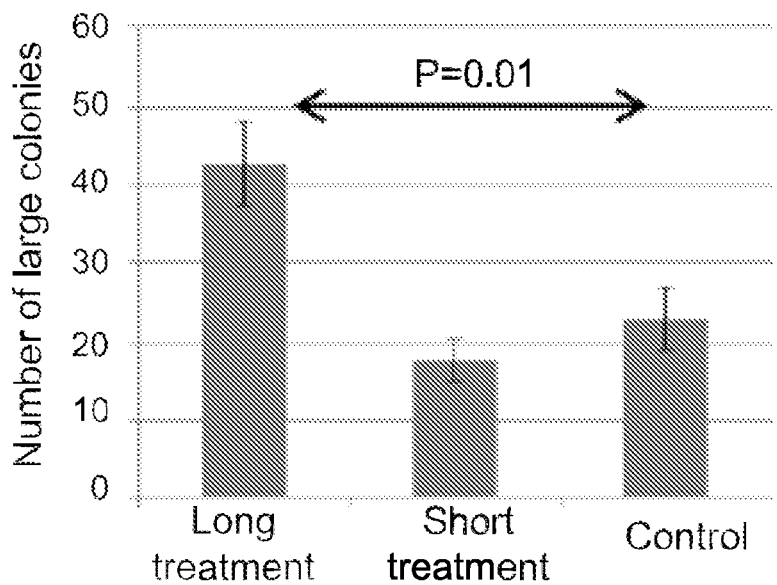
FIG. 4D is a graph showing the number of large colonies.
Figure 4E:
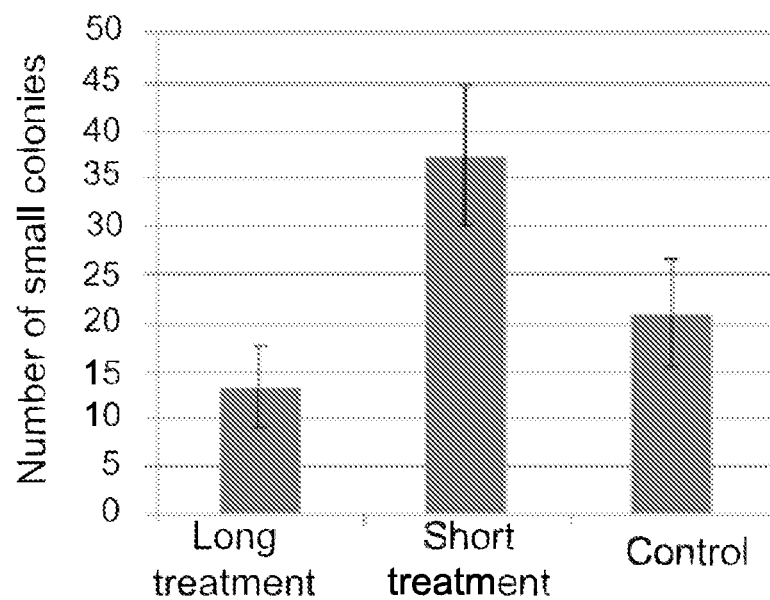
FIG. 4E is a graph showing the number of small colonies.
Figure 4F:
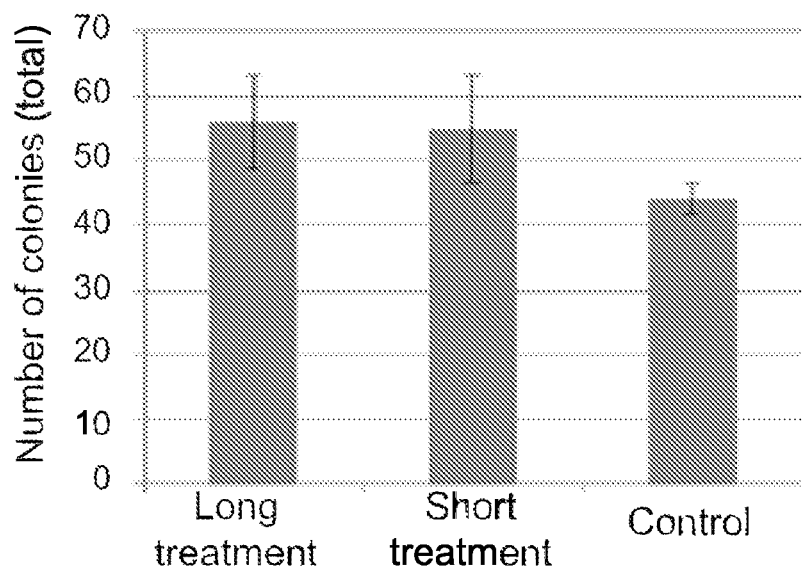
FIG. 4F is a graph showing the total number of colonies.

The number of colony forming units (CFU) in cultures that were incubated with FasL was then evaluated, as demonstrated in FIG. 4. For this assay cells were plated at a density of 2,000 cells per 6 cm dishes in triplicates. The cells were incubated in the presence of FasL for 20 days or for 3 days. At 20 days post seeding, Fas-ligand treated and untreated plates were fixed and stained with Giemsa. Large colonies of CFU (FIG. 4A) and small colonies of CFU (FIG. 4B) could be detected in the cultures.

As shown in FIG. 4C, colony forming units were formed under all of the assayed conditions. Apparently, the total number of colony forming units was higher in the treatment groups than in untreated cells, and was similar in cultures that were treated with FasL for a long treatment period (20 days) and for a short treatment period (3 days), as also shown in table 4 below.

Interestingly however, large colonies were formed in cells that were incubated with FasL for 20 days, whereas small colonies were formed in cells that were incubated with FasL for 3 days, as demonstrated in FIG. 4A and FIG. 4B, respectively.

Apparently, although the total number of CFU in cell cultures incubated in the presence of Fas-ligand for only 3 days was similar to the number of CFU in cell cultures incubated in the presence of Fas-ligand for 20 days, the percentage of large colonies was higher in cells that were incubated with FasL for 20 days, as shown in table 4 below.

TABLE 4

Number of large and small colonies formed

| | FASL treatment 20 days | FASL treatment 3 days | Untreated |
|---|---|---|---|
| Number of large colonies | 43 ± 5 | 18 ± 3 | 23 ± 4 |

TABLE 3

Expression of surface markers

| | Control (%) | | | FASL treatment 14 days (%) | | | FASL treatment 3 days (%) | | |
|---|---|---|---|---|---|---|---|---|---|
| Name | D 0 | D 14 | D 28 | D 0 | D 14 | D 28 | D 0 | D 14 | D 28 |
| $CD31^-CD34^-$ | 95 | 97 | 90 | 89 | 81 | 84 | 98 | 96 | 90 |
| $CD31^+CD34^-$ | 4.3 | 1.3 | 0.6 | 9 | 8.1 | 0.9 | 0.5 | 1.1 | 1.9 |
| $CD31^-CD34^+$ | 0.5 | 1.6 | 8.8 | 1.7 | 6.3 | 15 | 1.7 | 2.8 | 7.3 |
| $CD31^+CD34^+$ | 0.4 | 0.2 | 0.6 | 1.3 | 4.9 | 1.5 | 0.3 | 0.3 | 0.8 |
| $CD29^+CD105^+$ | 91.3 | 69 | 62 | 87 | 29.5 | 24.7 | 89 | 68.8 | 59 |
| $CD29^+CD105^-$ | 1.2 | 19.8 | 33.3 | 2.5 | 55.3 | 67 | 0.4 | 18.7 | 32 |
| $CD29^-CD105^+$ | 6.8 | 6.7 | 1.7 | 8.3 | 0.6 | 0.5 | 10 | 7.2 | 2.7 |
| $CD29^-CD105^-$ | 0.6 | 4.2 | 2.8 | 1.9 | 14 | 7.9 | 0.4 | 5.4 | 5.7 |

TABLE 4-continued

Number of large and small colonies formed

| | FASL treatment 20 days | FASL treatment 3 days | Untreated |
|---|---|---|---|
| Number of small colonies | 13 ± 4 | 37 ± 7 | 21 ± 6 |
| Total number of colonies | 56 ± 7 | 55 ± 8 | 44 ± 3 |

The number of colonies (CFU) was evaluated using microscope counting. These results are also demonstrated in FIG. 4D (the number of large colonies), FIG. 4E (the number of small colonies) and FIG. 4F (the total number of colonies).

From the above results it is evident that treatment with FasL for 20 days resulted in an increased number of large colonies compared to both untreated cells and cells that received treatment for only three days. In addition, cells that were treated with Fas-ligand for only three days were characterized by an increase in the number of small colonies compared to cells subjected to treatment with FasL for 20 days. Large colonies are known to be formed from early progenitor cells (e.g. stem and progenitor cells). It thus appears that FasL may preferentially support/select for early progenitor stem cells.

Approximately 2% of all cells develop into colonies.

Example 2 Induction of Differentiation

Bone Differentiation—

SVF cells from the fatty portion of liposuction aspirates were obtained and seeded as described above. The cells were then divided into two experimental groups: one group of cells was incubated in the presence of FasL (SuperFasL 50 ng/ml), and the second group was incubated without FasL, and served as a control.

After incubation of 7-10 days (with or without FasL), when the cell cultures reached confluence, the MSCs were cultured in various induction media in order to induce differentiation into bone cells or fat cells.

In one set of experiments, the MSCs were cultured in an osteogenesis induction medium, the StemPro® Osteogenesis Differentiation Kit (Gibco). This kit contains various reagents required for inducing differentiation in vitro of human mesenchymal stem cells into bone cells. The induction medium was replaced every 3-4 days in all cases.

Figure 5A:
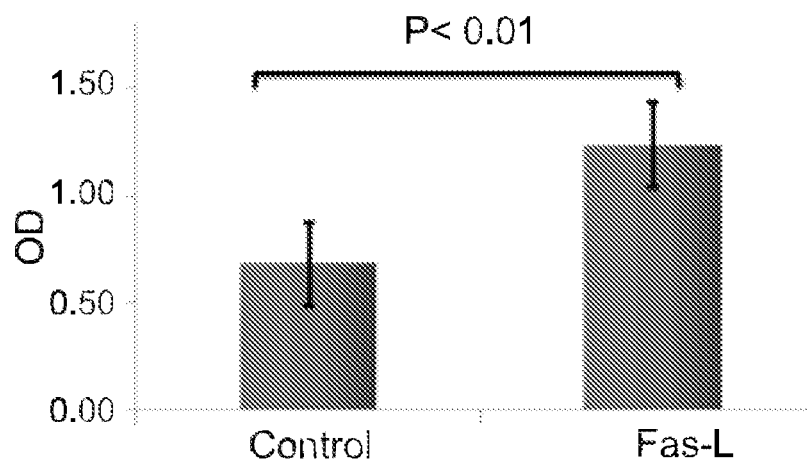
FIG. 5A is graph showing alizarin red staining of MSC grown in culture with an osteogenic medium. The cells were previously exposed to FasL, or unexposed (control). P<0.01, experiments were repeated three times.
Figures 5B, 5C:
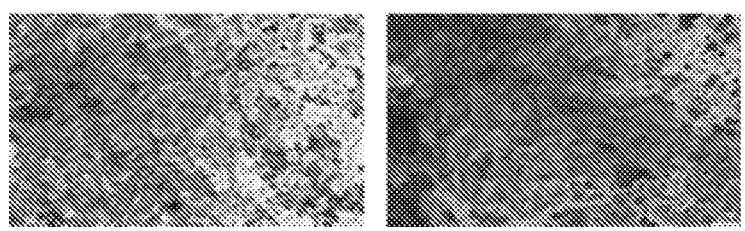
FIGS. 5B and 5C are photographs showing differentiated osteoblasts in culture stained with alizarin red.

After 21 days in the presence of the differentiation medium, the cells were fixed with 4% formalin (20 min at RT) and stained with 2% Alizarin Red (Sigma), pH 4.2 (10 min at RT). Alizarin red is a commonly used stain to identify calcium containing osteocytes in differentiated (nature of human mesenchymal stem cells. As can be seen in FIG. 5 FasL treated MSCs demonstrate bone differentiation superior to untreated control. Photographs were taken using an Olympus IX71 microscope with a DP51 camera.

Differentiation into Fat Cells—

In another set of experiments, the MSCs were cultured in an adipogenic medium containing 10 μg/mL insulin, 1×10-6M dexamethasone, 0.5 mM IBMX (3-isobutyl-1-methylxanthine) and 50 μM indomethacin (all from Sigma). After 21 days, the cells were fixed by 4% formalin (20 min at room temperature [RT]) and stained with 0.5% Oil Red O for 10 min, at RT) (Sigma). Oil Red O is commonly used for selective staining and detection of neutral lipids in cultured cells. As can be seen in FIG. 6 FasL treated MSCs demonstrate fat differentiation comparable to untreated control. Photographs were taken using an Olympus IX71 microscope with a DP51 camera.

Immunosupperssion—

Next, the immunosuppressive properties of the cells were examined to test whether growing the MSC in the presence of FasL affects their immunosuppressive characteristics.

The immunosuppressive properties of the cells were tested in an assay using primary mouse splenocytes. The mouse splenocytes were obtained using a standard protocol comprising mechanical grinding of the spleen and filtration through 100 μm strainer, the cells were subjected to a red blood cell (RBC) lysis buffer followed by washes with medium (RPMI). $0.3 \times 10^6$ cells were seeded per well (using a solution containing $3 \times 10^6$ million cells/ml RPMI) on confluent human MSC obtained as described above (namely, MSC that were grown with or without FasL). The control included splenocytes grown in the absence of MSC. The splenocytes were activated using a mouse anti-mouse CD3 monoclonal antibody (1 pg/ml) for 96 hours. Activation level of the splenocytes was determined by measuring the levels of IFN gamma secreted to the medium using an ELISA. The measurements were performed according to manufacturer's instructions (PeproTech). As shown in FIG. 7, both untreated MSCs and FasL-treated MSCs significantly attenuated IFN gamma secretion from activated splenocytes compared to activated splenocytes incubated without MSCs.

Apparently, FasL treatment does not impair MSCs immunosuppressive properties compared to control MSCs as determined by the splenocyte activation assay.

The invention claimed is:

1. A method for propagating adipose derived stem cells (ASC), the method comprising:
   (a) isolating stromal vascular fraction (SVF) cells from a liposuction aspirate; and
   (b) incubating the isolated cells obtained in (a) in a growth medium comprising Fas ligand (FasL) for between about 5 days and 23 days, wherein the concentration of FasL is in the range of 10 ng/ml to 60 ng/ml thereby propagating ASC and obtaining a cell population enriched with ASC.

2. The method of claim 1, wherein said growth medium further comprises an additional active agent selected from the group consisting of a growth factor, a hormone, a cytokine and any combination thereof.

3. The method of claim 1, wherein said incubation with FasL is for about 5, 7, 10, 14, 17, 20, or 23 days.

4. The method of claim 3, wherein said incubation with FasL is for 14 days.

5. The method according to claim 1, wherein after step (a) the isolated cells are cultured for 1, 2, 3, 4, 5, 6 or 7 days without Fas-ligand (FasL), followed by the incubation with Fas-ligand (FasL).

6. The method of claim 1, wherein the concentration of FasL is in the range of 20 ng/ml to 50 ng/ml.

* * * * *